US010881749B2

(12) United States Patent
Namavari et al.

(10) Patent No.: US 10,881,749 B2
(45) Date of Patent: *Jan. 5, 2021

(54) PROBES AND METHODS OF IMAGING A BACTERIAL INFECTION

(71) Applicant: The Board of Trustees of the Leland Stanford Junior University, Palo Alto, CA (US)

(72) Inventors: Mohammad Namavari, Palo Alto, CA (US); Gayatri Gowrishankar, Cupertino, CA (US); Sanjiv S. Gambhir, Portola Valley, CA (US); Ananth Srinivasan, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 325 days.

This patent is subject to a terminal disclaimer.

(21) Appl. No.: 15/096,308

(22) Filed: Apr. 12, 2016

(65) Prior Publication Data

US 2016/0303259 A1 Oct. 20, 2016

Related U.S. Application Data

(60) Provisional application No. 62/148,798, filed on Apr. 17, 2015.

(51) Int. Cl.
| | | |
|---|---|---|
| *A61K 51/04* | (2006.01) | |
| *A61K 51/06* | (2006.01) | |
| *C07H 15/04* | (2006.01) | |
| *C07H 7/02* | (2006.01) | |
| *C07B 59/00* | (2006.01) | |

(52) U.S. Cl.
CPC .......... *A61K 51/0491* (2013.01); *A61K 51/06* (2013.01); *C07B 59/005* (2013.01); *C07H 7/02* (2013.01); *C07H 15/04* (2013.01); *C07B 2200/05* (2013.01)

(58) Field of Classification Search
None
See application file for complete search history.

(56) References Cited

FOREIGN PATENT DOCUMENTS

WO    WO-2012097223 A2 *    7/2012    .......... A61K 47/4823

OTHER PUBLICATIONS

Dippel et al. The maltodextrin system of *Escherichia coli*: metabolism and transport. 2005 J. Bacteriol. 187: 8322-8331. (Year: 2005 ).*
Malik et al. Maltose and maltotriose derivatives as potential inhibitors of the maltose-binding protein. 2008 Eur. J. Org. Chem. 12: 2084-2099. (Year: 2008).*

* cited by examiner

*Primary Examiner* — Jennifer Lamberski
(74) *Attorney, Agent, or Firm* — Thomas | Horstemeyer, LLP

(57) ABSTRACT

Embodiments of the present disclosure provide for labeled probes such as labeled maltoside probes and labeled maltotriose probes, methods of making labeled probes, pharmaceutical compositions including labeled probes, methods of using labeled probes, methods of diagnosing, localizing, monitoring, and/or assessing bacterial infections, using labeled probes, kits for diagnosing, localizing, monitoring, and/or assessing bacterial infections, using labeled probes, and the like.

5 Claims, 7 Drawing Sheets

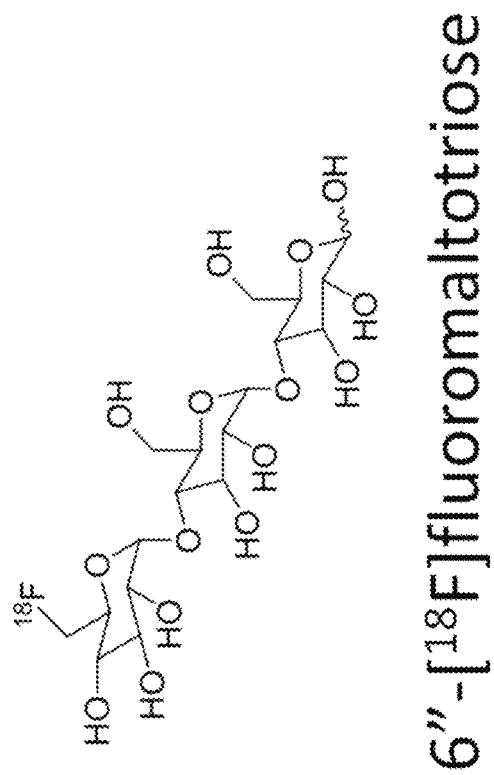
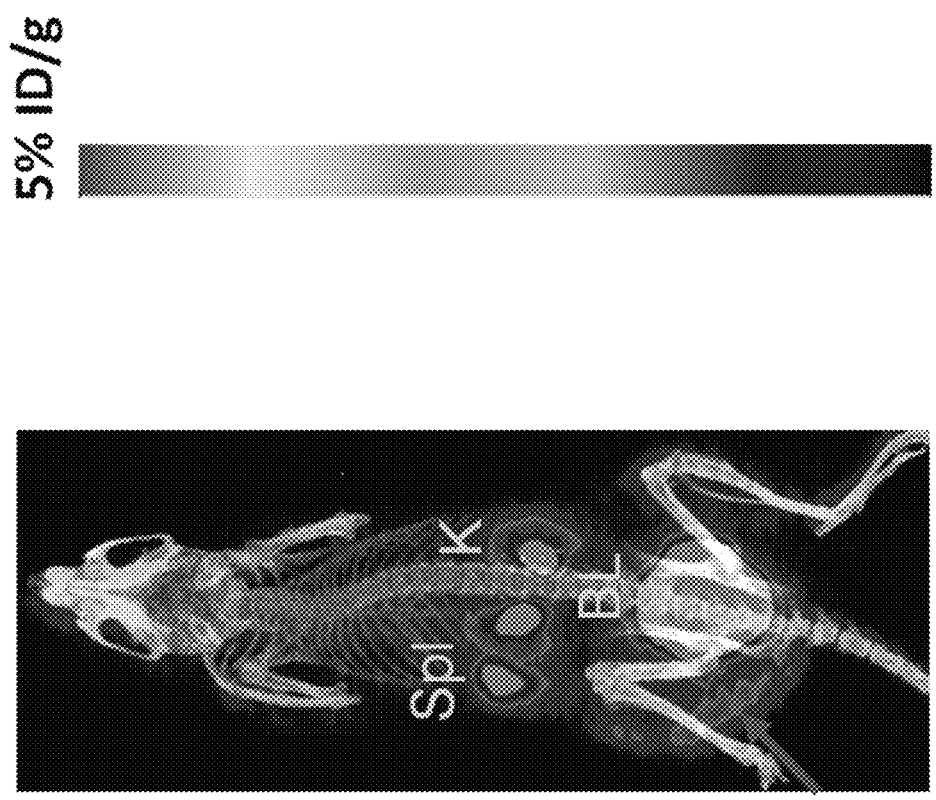
Fig. 1.1A
Fig. 1.1B

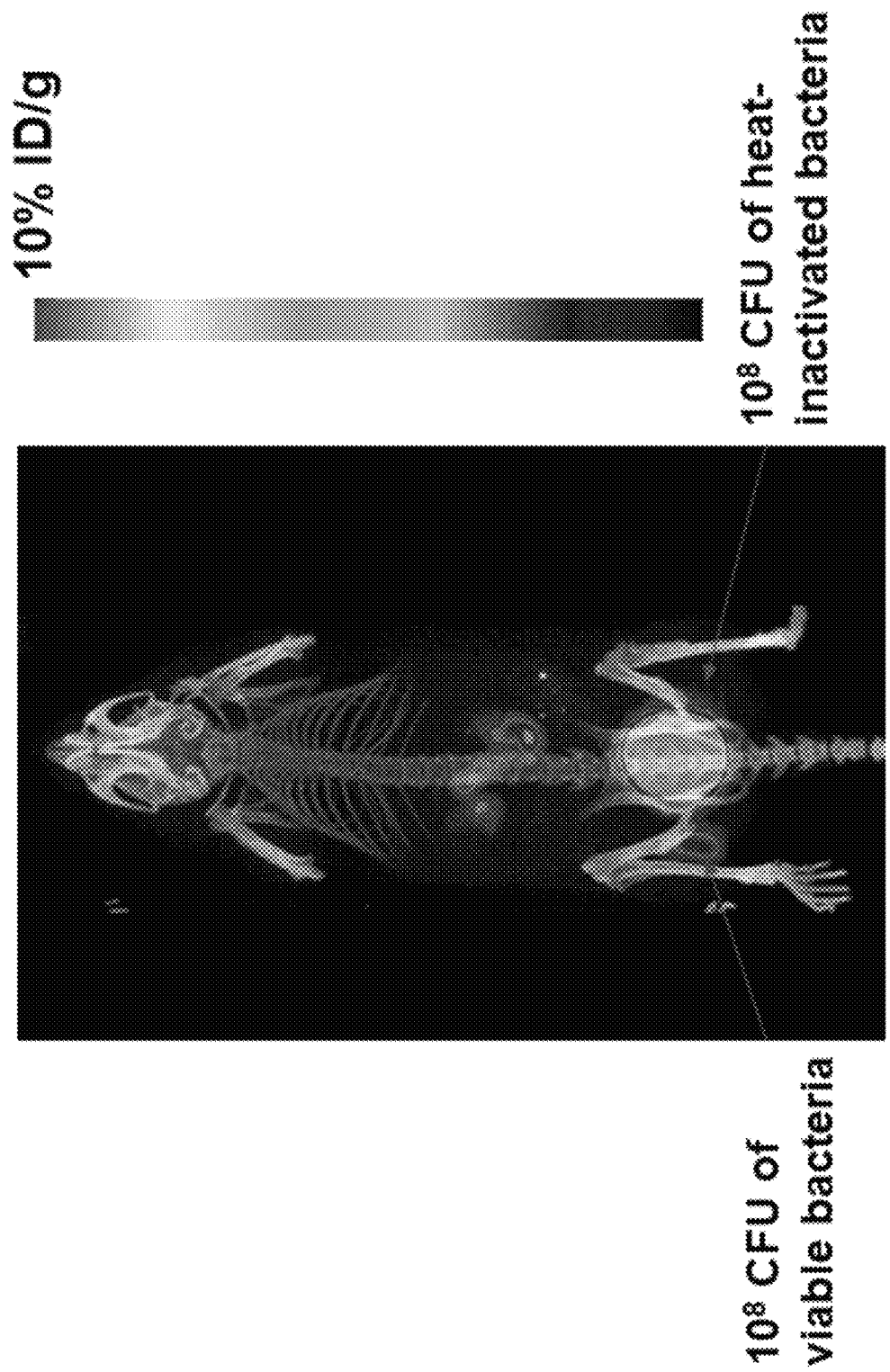
Fig. 1.2

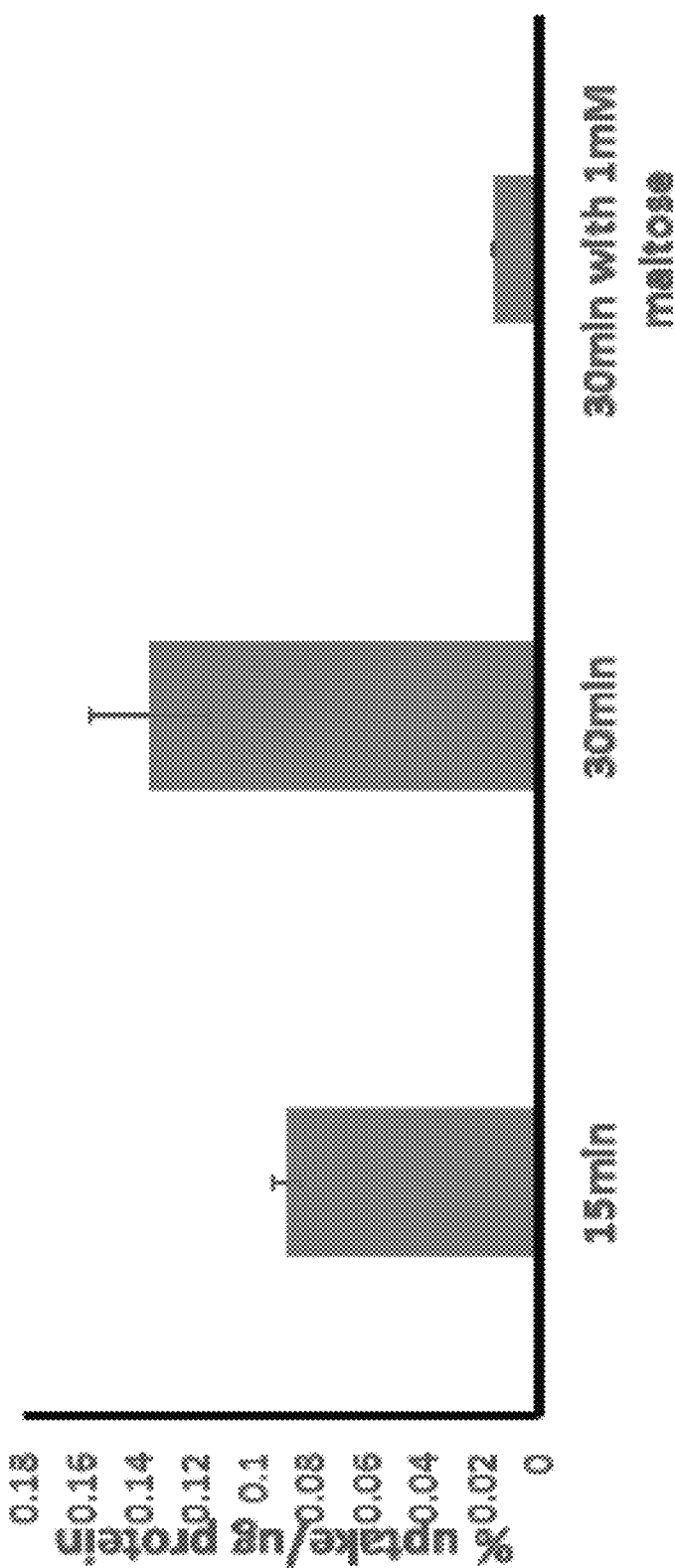
Fig. 2.1

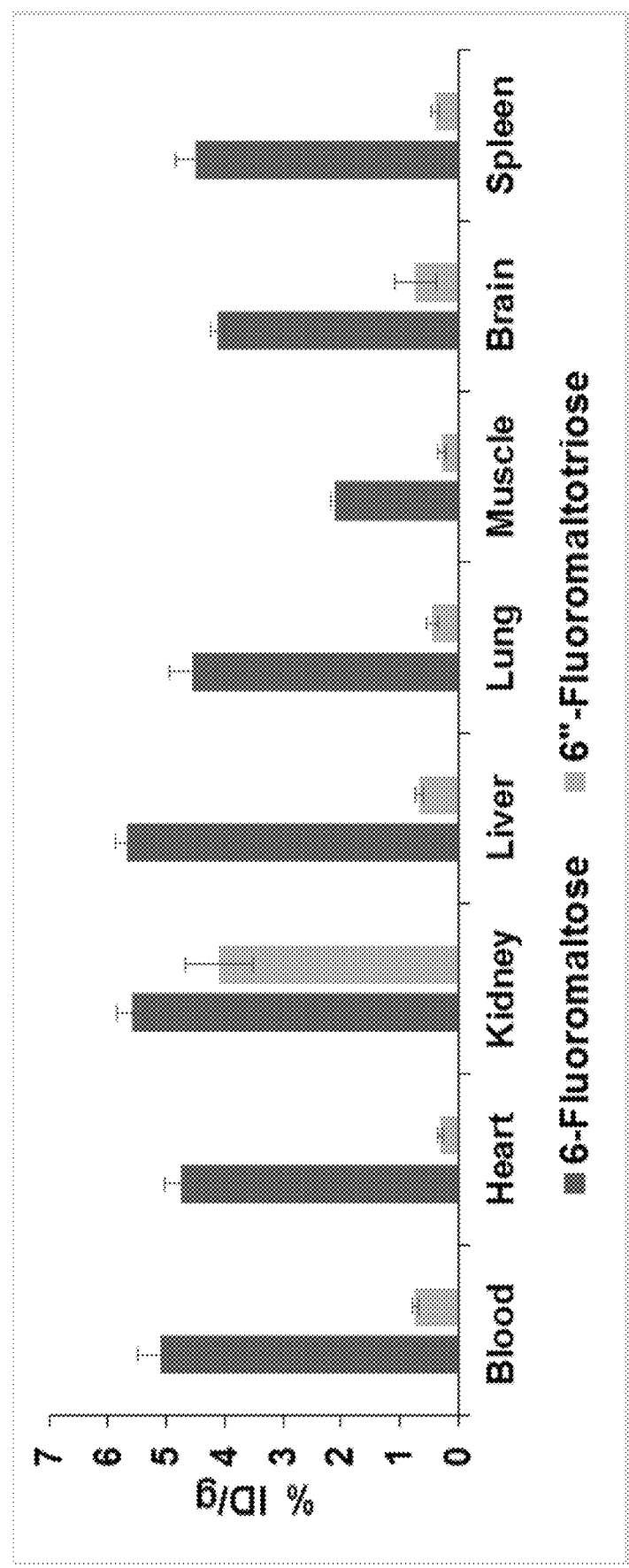
Fig. 3.1

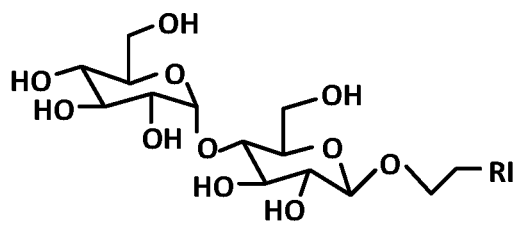
1-RI-ethylmaltoside
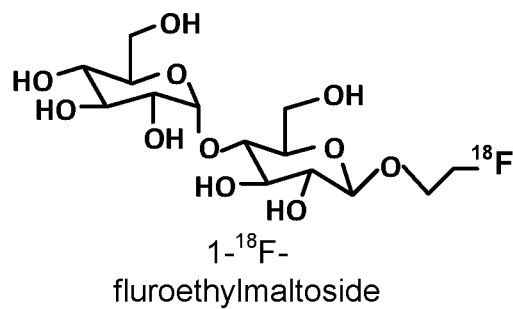
1-$^{18}$F-fluroethylmaltoside
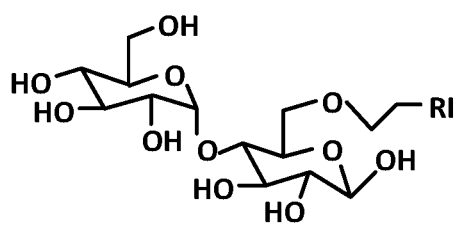
6-RI-ethylmaltoside
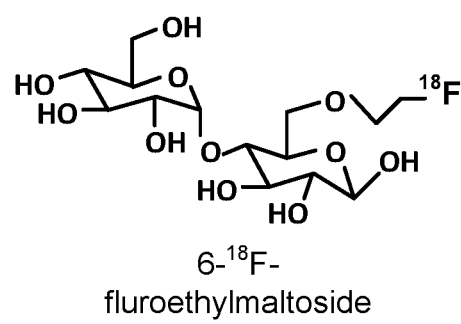
6-$^{18}$F-fluroethylmaltoside
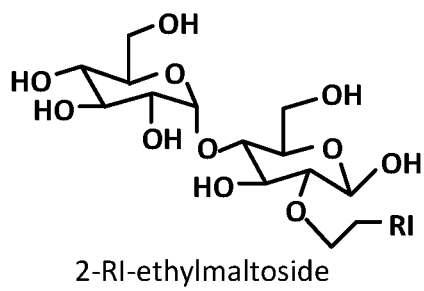
2-RI-ethylmaltoside
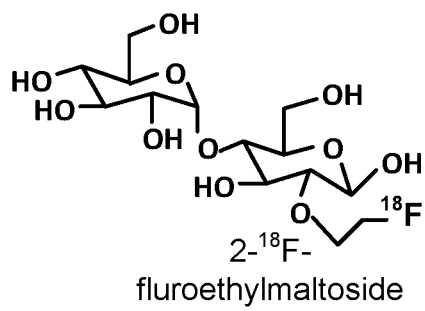
2-$^{18}$F-fluroethylmaltoside
Fig. 4.1A

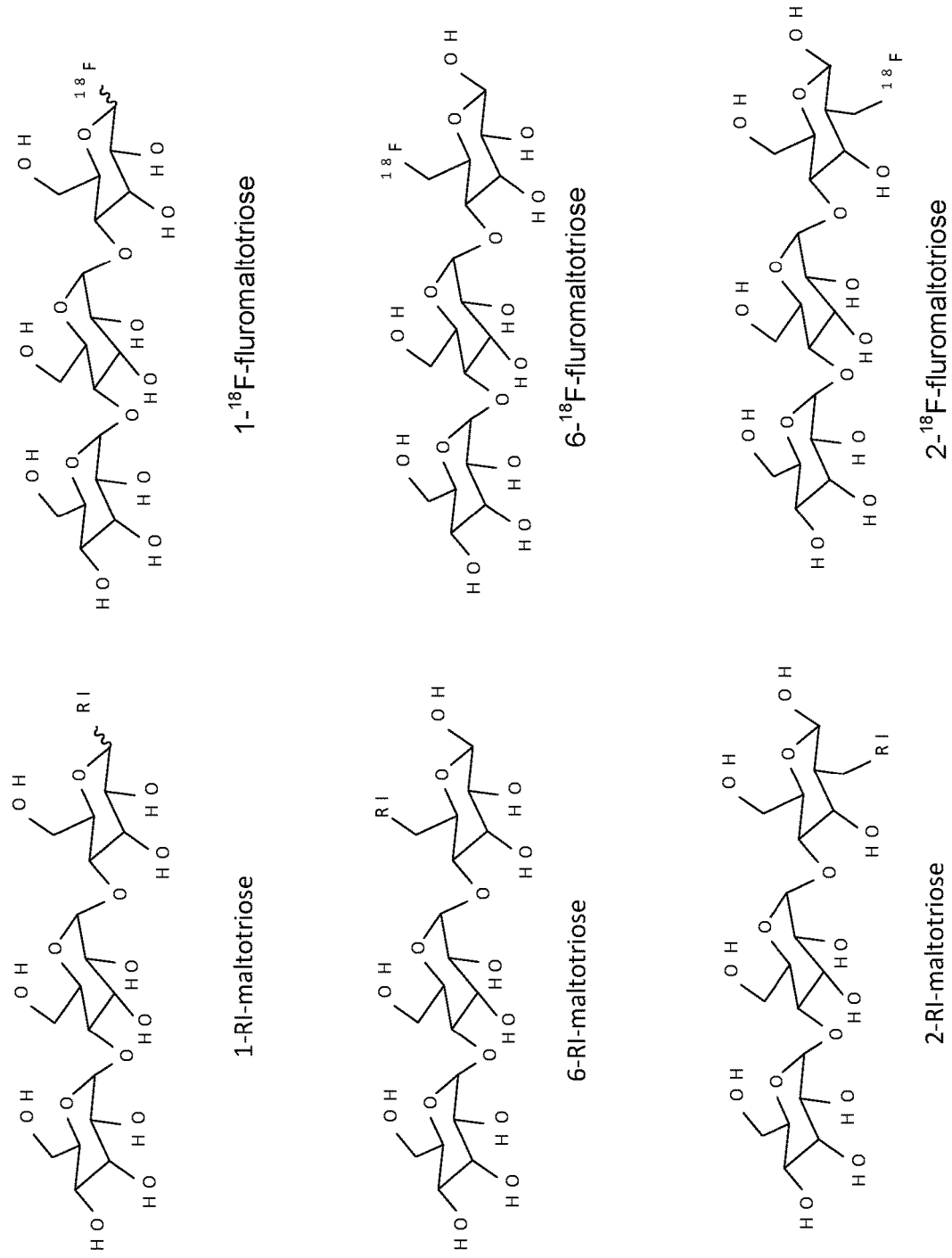
Fig. 4.1B

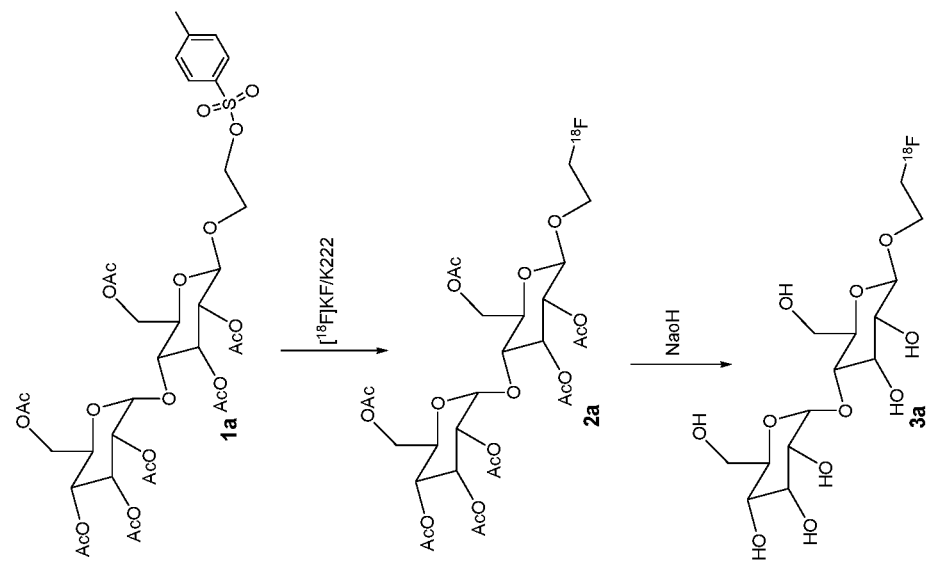
Fig. 5.1C Scheme 3: Synthesis of 1-ethyl fluoromaltoside (3a)
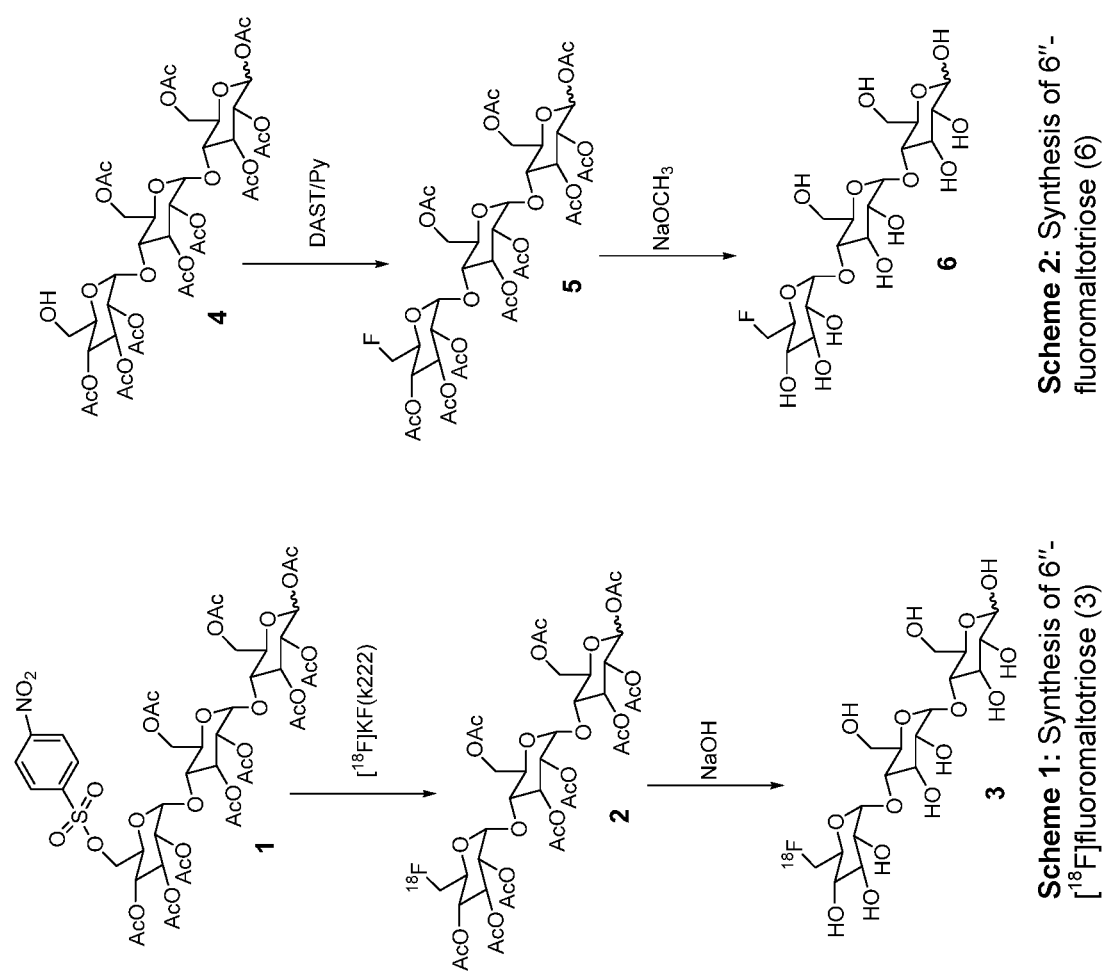
Fig. 5.1B Scheme 2: Synthesis of 6''-fluoromaltotriose (6)
Fig. 5.1A Scheme 1: Synthesis of 6''-[18F]fluoromaltotriose (3)

PROBES AND METHODS OF IMAGING A BACTERIAL INFECTION

CROSS-REFERENCE TO RELATED APPLICATIONS

This application claims the benefit of and priority to U.S. Provisional Application Ser. No. 62/148,798, having the title "PROBES AND METHODS OF IMAGING A BACTERIAL INFECTION," filed on Apr. 17, 2015, the disclosure of which is incorporated herein in by reference in its entirety.

BACKGROUND

Early detection of bacterial infection is correlated with greater prognosis for full recovery. Conventional anatomic imaging techniques such as magnetic resonance imaging (MRI) and computed tomography (CT) are incapable of reliably distinguishing infection from sterile inflammation. Thus, there is a need to overcome these deficiencies.

SUMMARY

Embodiments of the present disclosure provide for labeled probes such as labeled maltoside probes and labeled maltotriose probes, methods of making labeled probes, pharmaceutical compositions including labeled probes, methods of using labeled probes, methods of diagnosing, localizing, monitoring, and/or assessing bacterial infections, using labeled probes, kits for diagnosing, localizing, monitoring, and/or assessing bacterial infections, using labeled probes, and the like.

An exemplary embodiment of the present disclosure includes a method of imaging a bacterial infection in a subject, among others, that includes: administering to the subject a labeled probe selected from the group consisting of: a labeled maltoside probe and a labeled maltotriose probe; imaging at least a portion of the subject; and detecting the labeled probe, wherein the location of the labeled probe corresponds to bacterial infection.

An exemplary embodiment of the present disclosure includes a composition, among others, that includes: a labeled probe, wherein the labeled probe is selected from: 1-RI-ethyl maltoside, 2-RI-ethyl maltoside, 6-RI-ethyl maltoside, 6'-RI-ethyl maltoside, 1-RI-maltotriose, 2-RI-maltotriose, 6-RI-maltotriose, 6'-RI-maltotriose, or 6"-RI-maltotriose, wherein RI is a radiolabel.

Other compositions, methods, features, and advantages will be or become apparent to one with skill in the art upon examination of the following drawings and detailed description. It is intended that all such additional compositions, apparatus, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure.

FIGS. 1.1A-B show PET/CT scan of a mouse that had been injected with 200 µCi of 6"-[$^{18}$F]-fluoromaltotriose. The arrow indicates the site of infection. Kidney (K), Bladder (BL) and spleen (Spl) are also shown in the figure.

FIG. 1.2 illustrates that 6"-[$^{18}$F]-fluoromaltotriose can image 10$^8$ CFU of viable bacteria 2 hours after implantation with exquisite specificity.

FIG. 2.1 is a graph showing uptake of 6"-[$^{18}$F]fluoromaltotriose in vitro in E coli at 15 minutes, 30 minutes, and 30 minutes with 1 mM of maltose.

FIG. 3.1 illustrates a graph comparing the biodistribution and pharmacokinetics of 6-fluoromaltose and 6"-fluoromaltotriose in mice.

FIGS. 4.1A and 4.1B illustrate embodiments of the present disclosure.

FIGS. 5.1A and 5.1B illustrate embodiments of methods of making an embodiment of a labeled maltotriose probe (the 6" position is shown below). FIG. 5.1C illustrates an embodiment of a method of making an embodiment of a labeled ethyl maltoside probe (the 1 position is shown below).

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, molecular imaging, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

In describing and claiming the disclosed subject matter, the following terminology will be used in accordance with the definitions set forth below.

By "administration" or "administering" is meant introducing a probe or a labeled probe (also referred to as the "imaging agent") (e.g., [18F]-ethyl maltoside probe or [18F]-maltotriose) of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid, or instillation into body compartments can be used.

In accordance with the present disclosure, "a detectably effective amount" of the labeled probe of the present disclosure is defined as an amount sufficient to yield an acceptable image using equipment that is available for clinical use. A detectably effective amount of the labeled probe of the present disclosure may be administered in more than one injection. The detectably effective amount of the labeled probe of the present disclosure can vary according to factors such as the degree of susceptibility of the individual, the age, sex, and weight of the individual, idiosyncratic responses of the individual, and the like. Detectably effective amounts of the probe of the present disclosure can also vary according to instrument and film-related factors. Optimization of such factors is well within the level of skill in the art.

As used herein, the term "subject" includes vertebrates such as humans and mammals (e.g., cats, dogs, horses, etc.) and ayes. Typical hosts to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a host. The term "living subject" refers to a subject noted above that is alive and is not dead. The term "living subject" refers to the entire subject and not just a part excised (e.g., a liver or other organ) from the living subject.

The term "sample" can refer to a tissue sample, cell sample, a fluid sample, and the like. The sample may be taken from a subject. The tissue sample can include hair (including roots), buccal swabs, blood, saliva, semen, muscle, or from any internal organs. The fluid may be, but is not limited to, urine, blood, ascites, pleural fluid, spinal fluid, and the like. The body tissue can include, but is not limited to, skin, muscle, endometrial, uterine, and cervical tissue. In the present disclosure, the source of the sample is not critical.

The term "detectable" refers to the ability to detect a signal over the background signal.

The term "detectable signal" is a signal derived from non-invasive imaging techniques such as, but not limited to, positron emission tomography (PET). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

The phrase "bacterial infection" can refer to a bacteria colonizing a tissue or organ of a subject, where the colonization causes harm to the subject. The harm can be caused directly by the bacteria and/or by toxins produced by the bacteria. Reference to bacterial infection includes also includes bacterial disease.

Bacteria that cause bacterial infections are called pathogenic bacteria. The terms "bacteria" or "bacterium" include, but are not limited to, Gram positive and Gram negative bacteria. Bacteria can include, but are not limited to, *Abiotrophia, Achromobacter, Acidaminococcus, Acidovorax, Acinetobacter, Actinobacillus, Actinobaculum, Actinomadura, Actinomyces, Aerococcus, Aeromonas, Afipia, Agrobacterium, Alcaligenes, Alloiococcus, Alteromonas, Amycolata, Amycolatopsis, Anaerobospirillum, Anabaena affinis* and other cyanobacteria (including the *Anabaena, Anabaenopsis, Aphanizomenon, Camesiphon, Cylindrospermopsis, Gloeobacter Hapalosiphon, Lyngbya, Microcystis, Nodularia, Nostoc, Phormidium, Planktothrix, Pseudoanabaena, Schizothrix, Spirulina, Trichodesmium,* and *Umezakia* genera) *Anaerorhabdus, Arachnia, Arcanobacterium, Arcobacter, Arthrobacter, Atopobium, Aureobacterium, Bacteroides, Balneatrix, Bartonella, Bergeyella, Bifidobacterium, Bilophila Branhamella, Borrelia, Bordetella, Brachyspira, Brevibacillus, Brevibacterium, Brevundimonas, Brucella, Burkholderia, Buttiauxella, Butyrivibrio, Calymmatobacterium, Campylobacter, Capnocytophaga, Cardiobacterium, Catonella, Cedecea, Cellulomonas, Centipeda, Chlamydia, Chlamydophila, Chromobacterium, Chyseobacterium,*

*Chryseomonas, Citrobacter, Clostridium, Collinsella, Comamonas, Corynebacterium, Coxiella, Cryptobacterium, Delftia, Dermabacter, Dermatophilus, Desulfomonas, Desulfovibrio, Dialister, Dichelobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Gemella, Globicatella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Phytoplasma, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea Roseomonas, Rothia, Ruminococcus, Salmonella, Selenomonas, Serpulina, Serratia, Shewenella, Shigella, Simkania, Slackia, Sphingobacterium, Sphingomonas, Spirillum, Spiroplasma, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella*. Other examples of bacterium include *Mycobacterium tuberculosis, M. bovis, M. typhimurium, M. bovis* strain BCG, BCG substrains, *M. avium, M. intracellulare, M. africanum, M. kansasii, M. marinum, M. ulcerans, M. avium* subspecies paratuberculosis, *Staphylococcus aureus, Staphylococcus epidermidis, Staphylococcus equi, Streptococcus pyogenes, Streptococcus agalactiae, Listeria monocytogenes, Listeria ivanovii, Bacillus anthracis, B. subtilis, Nocardia asteroides,* and other *Nocardia* species, *Streptococcus viridans* group, *Peptococcus* species, *Peptostreptococcus* species, *Actinomyces israelii* and other *Actinomyces* species, and *Propionibacterium acnes, Clostridium tetani, Clostridium botulinum,* other *Clostridium* species, *Pseudomonas aeruginosa,* other *Pseudomonas* species, *Campylobacter* species, *Vibrio cholera, Ehrlichia* species, *Actinobacillus pleuropneumoniae, Pasteurella haemolytica, Pasteurella multocida,* other *Pasteurella* species, *Legionella pneumophila,* other *Legionella* species, *Salmonella typhi,* other *Salmonella* species, *Shigella* species *Brucella abortus,* other *Brucella* species, *Chlamydi trachomatis, Chlamydia psittaci, Coxiella burnetti, Escherichia coli, Neiserria meningitidis, Neiserria gonorrhea, Haemophilus influenzae, Haemophilus ducreyi,* other *Hemophilus* species, *Yersinia pestis, Yersinia enterolitica,* other *Yersinia* species, *Escherichia coli, E. hirae* and other *Escherichia* species, as well as other *Enterobacteria, Brucella abortus* and other *Brucella* species, *Burkholderia cepacia, Burkholderia pseudomallei, Francisella tularensis, Bacteroides fragilis, Fudobascterium nucleatum, Provetella* species, and *Cowdria ruminantium,* or any strain or variant thereof. The Gram-positive bacteria may include, but is not limited to, Gram positive Cocci (e.g., *Streptococcus, Staphylococcus,* and *Enterococcus*). The Gram-negative bacteria may include, but is not limited to, Gram negative rods (e.g., Bacteroidaceae, Enterobacteriaceae, Vibrionaceae, Pasteurellae and Pseudomonadaceae).

General Discussion

Embodiments of the present disclosure provide for labeled probes such as labeled maltoside probes and labeled maltotriose probes, methods of making labeled probes, pharmaceutical compositions including labeled probes, methods of using labeled probes, methods of diagnosing, localizing, monitoring, and/or assessing bacterial infections, using labeled probes, kits for diagnosing, localizing, monitoring, and/or assessing bacterial infections, using labeled probes, and the like.

Embodiments of the present disclosure are advantageous for at least the following reasons. Maltose is used in pathways of multiple types of pathogenic bacteria (e.g., *Pseudomonas aeruginosa, Escherichia coli, Bacillus subtilis, Streptococcus pneumoniae, Staphylococcus aureus,* and *Listeria monocytogenes*). Maltose is taken up at a rate of ten times that of glucose, and maltose is not taken up by mammalian cells. An advantage of using labeled maltose-like probes (e.g., labeled ethyl maltoside probes and labeled maltotriose probes) is that it is a specific substrate for bacteria and can be used to image bacterial infections in mammals. Also, maltose transporters are present in most pathogenic bacteria, so labeled probes can be used to image multiple types of infections and/or differentiate between bacterial and viral infections. Ethyl maltoside and maltotriose are pseudooligosaccharides, which are transported but not metabolized by the maltose-maltodextrine system of *E. coli*.

In an embodiment, the labeled probe can be used to image bacterial infections such as those from *Pseudomonas aeruginosa*. In particular, the present disclosure includes methods relating to non-invasive imaging (e.g., using positron emission tomography (PET) imaging system) using labeled maltoside probes, such as a 1-$^{18}$F-ethyl maltoside probe, 2-$^{18}$F-ethyl maltoside probe, 6-$^{18}$F-ethyl maltoside probe and 6'-$^{18}$F-ethyl maltoside probe, and labeled maltotriose probes, such as 1-$^{18}$F-maltotriose probe, 2-$^{18}$F-maltotriose probe, 6-$^{18}$F-maltotriose probe, 6'-$^{18}$F-maltotriose probe and 6"-$^{18}$F-maltotriose probe, in vivo. Additional details are described in the Examples.

Embodiments of the present disclosure include methods for imaging a sample (e.g., tissue or cell(s)) or a subject (e.g., mammal), that includes contacting a sample with or administering to a subject a labeled probe (e.g., [18F]-ethyl maltoside probe and [18F]-maltotriose probe) and imaging with a PET imaging system. The imaging can be performed in vivo and/or in vitro. In particular, embodiments of the present disclosure can be used to image bacterial infection. In this regard, the sample or subject can be tested to determine if the sample or subject includes a bacterial infection, monitor the progression (or regression) of the bacterial infection, assess the response of the bacterial infection to treatment, and the like. In an embodiment, the tissue or cells can be within a subject or have been removed from a subject.

In an embodiment, the labeled probe (e.g., [$^{18}$F]-ethyl maltoside probe and [$^{18}$F]-maltotriose probe) can be imaged using imaging systems such as positron emission tomography (PET) imaging systems. In an embodiment, PET imaging is a preferred embodiment. Other types of labeled maltoside probes can use appropriate imaging systems.

In an embodiment, the labeled probe can be used in diagnosing, localizing, monitoring, and/or assessing bacterial infections. In particular, the present disclosure includes methods relating to non-invasive imaging (e.g., using positron emission tomography (PET) imaging system) using the labeled probe in vivo.

Embodiments of the present disclosure can be used to target bacteria, in particular, bacterial infections, in a subject such as a mammal, specifically, a human, since mammalian cells do not take up the labeled probe and the pathogenic bacteria takes up the labeled probe.

In an embodiment, the labeled probe can include a radiolabeled ethyl maltoside probe or radiolabeled maltotriose probe. In an embodiment, the radiolabeled ethyl maltoside probe or radiolabeled maltotriose probe can have one of the structures as shown in FIGS. 4.1A and 4.1B.

RI stands for radioisotope and is also referred to as a radiolabel. In an embodiment, the radiolabel can include one of the following: $^{18}F$, $^{125}I$, $^{124}I$, $^{131}I$, $^{123}I$, $^{32}Cl$, $^{33}Cl$, $^{34}Cl$, $^{74}Br$, $^{78}Br$, $^{76}Br$, $^{77}Br$, $^{78}Br$, $^{11}C$, or $^{68}G$. In an embodiment, the radiolabel can be $^{18}F$. In an embodiment, the radiolabel can be positioned at the 1, 2, 6, 6', or 6" position of the ethyl maltoside or maltotriose structure. In an embodiment, the labeled maltoside probe can include: 1-RI-ethyl maltoside probe, 2-RI-ethyl maltoside probe, 6-RI-ethyl maltoside probe and 6'-RI-ethyl maltoside probe. In an embodiment, the labeled maltoside probe can include: 1-$^{18}F$-ethyl maltoside probe, 2-$^{18}F$-ethyl maltoside probe, 6-$^{18}F$-ethyl maltoside probe and 6'-$^{18}F$-ethyl maltoside probe. In an embodiment, the labeled maltotriose probe can include: 1-RI-maltotriose probe, 2-RI-maltotriose probe, 6-RI-maltotriose probe, 6'-RI maltotriose probe or 6"-RI-maltotriose probe. In an embodiment, the labeled maltotriose probe can include: 1-$^{18}F$-maltotriose probe, 2-$^{18}F$-maltotriose probe, 6-$^{18}F$-maltotriose probe, 6'-$^{18}F$-maltotriose probe or 6"-$^{18}F$-maltotriose probe. In an embodiment, the radiolabel can include $^{11}C$, which can be any one of the carbon atoms or at the position of the RI (e.g., $^{11}CH_3$,) for either the radiolabeled ethyl maltoside probe or a radiolabeled maltotriose probe.

In an embodiment, each of the 1-$^{18}F$-ethyl maltoside probe, 2-$^{18}F$-ethyl maltoside probe, 6-$^{18}F$-ethyl maltoside probe or the 6'-$^{18}F$-ethyl maltoside probe, and the 1-$^{18}F$-maltotriose probe, 2-$^{18}F$-maltotriose probe, or the 6-$^{18}F$-maltotriose probe, 6'-$^{18}F$-maltotriose probe, 6"-$^{18}F$-maltotriose probe includes a label, $^{18}F$, that can be used to detect, image, or otherwise identify the probe, quantify the amount of the probe, determine the location of the probe (e.g., in imaging), and combinations thereof. As noted above, these labeled probes can be associated and/or correlated with a bacterial infection, thus the detection of the probe in a location can be used to identify the location of the bacterial infection. Additional details regarding the labeled maltoside probe are described herein.

Embodiments of the labeled maltotriose probes can be made using the synthesis shown FIGS. 5.1A and 5.1B, where the radiolabels can be position at the 1, 2, or 6, 6', 6" position (the 6" position as shown in FIGS. 5.1A and 5.1B).

Embodiments of the labeled ethyl maltoside probes can be made using the synthesis shown in FIG. 5.1C, where the radiolabels can be positioned at the 1, 2, 6 or 6' position (the 1 position as shown in FIG. 5.1C).

In an embodiment, the method can include synthesizing [$^{18}F$]-1-fluoroethyl maltoside 3a from precursor per-O-acetyl-1-deoxy-ethyl-tosyl-maltose (1a) (FIG. 5.1c). [$^{18}F$]-labeled ethyl maltoside derivative 2a was prepared by nucleophilic reaction of tosylate group in 1a with anhydrous [$^{18}F$]KF/Kryptofix 2.2.2 in DMF at 100° C. for 20 min. Initial purification of [$^{18}F$]2a was performed via a light C-18 Sep-pack cartridge. After passing a solution of [$^{18}F$]2a in acetonitrile through a light neutral alumina Sep-pack and evaporating the solvent, it was smoothly hydrolyzed t by a base (1N NaOH) at 110° C. for 20 min and then neutralized by 1N HCl to yield [$^{18}F$]-1-fluoroethyl maltoside 3a. The radiochemical yield is about 8-10%. This synthesis can be generally applied to each of the embodiments of the radiolabeled ethyl maltoside probe or radiolabeled maltotriose probe.

In each synthesis, it should be noted that alternative protecting groups can be used to replace the acetyl group, the trityl group, and/or nosylate group so as long as any replacement(s) permit the synthesis to produce the desired labeled probe. For example, the acetyl group can be replaced with one of the following: benzoyl, benzyl, methoxymethyl, allyl, t-butyldimethylsilyl, tetrahydropyranyl, t-butyldiphenylsilyl and t-butyl; the trityl group can be replaced with one of the following: methoxyphenyldiphnylmethyl, t-butyldimethylsilyl, tetrahydropyranyl, t-butyldiphenylsilyl and t-butyl; and the nosylate group can be replaced with one of the following: tosylate, triflate, brosylate, mesylate, and thiolate groups.

It should be noted that portions of the present disclosure discuss labeled ethyl maltoside probes and labeled maltotriose probes while other portions describe a specific embodiment of the labeled ethyl maltoside probes and labeled maltotriose probes. Discussions focusing on the labeled ethyl maltoside probes and labeled maltotriose probes are not limiting to the scope of the disclosure, rather those discussions are merely describing an exemplary embodiment of the present disclosure.

Methods of Use

Embodiments of this disclosure include, but are not limited to: methods of imaging a sample or a subject using the labeled probe (e.g., [$^{18}F$]-ethyl maltoside probe or [$^{18}F$]-maltotriose probe); methods of imaging a bacterial infection, using the labeled probe (e.g., ethyl maltoside probe or [$^{18}F$]-maltotriose probe); methods of diagnosing a bacterial infection using the labeled probe (e.g., [$^{18}F$]-ethyl maltoside probe or [$^{18}F$]-maltotriose probe); methods of monitoring the progress of a bacterial infection using the labeled probe (e.g., [$^{18}F$]-ethyl maltoside probe or [$^{18}F$]-maltotriose probe), and the like.

Embodiments of the present disclosure can be used to image, detect, study, monitor, evaluate, assess, and/or screen, a bacterial infection in vivo or in vitro using the labeled probe (e.g., [$^{18}F$]-ethyl maltoside probe or [$^{18}F$]-maltotriose probe). Although reference below is made to the use of the [$^{18}F$]-ethyl maltoside probe or [$^{18}F$]-maltotriose probe, other labeled probes described herein can be used in the alternative.

In a particular embodiment, the [$^{18}F$]-maltotriose probe can be used in imaging a bacterial infection. For example, the [$^{18}F$]-maltotriose probe is provided or administered to a subject in an amount effective to result in uptake of the [$^{18}F$]-maltotriose probe into the bacterial infection. The subject is then introduced to an appropriate imaging system (e.g., PET system) for a certain amount of time (e.g., this depends on radioisotope being used). The bacterial infection that takes up the [$^{18}F$]-maltotriose probe could be detected using the imaging system. The location of the detected signal from the [$^{18}F$]-maltotriose probe can be correlated with the location of bacterial infection. In an embodiment, the dimensions of the location can be determined as well. Other labeled probes and labeled ethyl maltoside probes can be used in a similar manner.

In an embodiment, the steps of this method can be repeated at determined intervals so that the location and/or size of the bacterial infection can be monitored as a function of time and/or treatment. In particular, the [$^{18}$F]-maltotriose probe can find use in a host undergoing treatment, to aid in visualizing the response of bacterial infection to the treatment. In this embodiment, the [$^{18}$F]-maltotriose probe is typically visualized and sized prior to treatment, and periodically (e.g., hourly, daily, weekly, monthly, intervals in between these, and the like) during treatment, to monitor the bacterial infection. Other labeled probes and ethyl maltoside probes can be used in a similar manner.

Embodiments of the [$^{18}$F]-maltotriose probe also find use as a screening tool in vitro to select compounds for use in treating bacterial infection. The bacterial infection could be easily monitored by incubating the cells with the bacterial infection with the [$^{18}$F]-maltotriose probe during or after incubation with one or more candidate drugs. The ability of the drug compound to affect the disease can be imaged over time using the [$^{18}$F]-maltotriose probe. In other words, the efficacy of the candidate drugs can be monitored using probes of the present disclosure. Other labeled probes and ethyl maltoside probes can be used in a similar manner.

It should be noted that the amount effective to result in uptake of the labeled probe (e.g., [$^{18}$F]-maltotriose probe) into the cells or tissue of interest may depend upon a variety of factors, including for example, the age, body weight, general health, sex, and diet of the host; the time of administration; the route of administration; the rate of excretion of the specific probe employed; the duration of the treatment; the existence of other drugs used in combination or coincidental with the specific composition employed; and like factors well known in the medical arts.

Kits

The present disclosure also provides packaged compositions or pharmaceutical compositions comprising a pharmaceutically acceptable carrier and a labeled probe (e.g., [$^{18}$F]-ethyl maltoside probe or [$^{18}$F]-maltotriose probe) of the disclosure. In certain embodiments, the packaged compositions or pharmaceutical composition includes the reaction precursors to be used to generate the labeled probe according to the present disclosure. Other packaged compositions or pharmaceutical compositions provided by the present disclosure further include material including at least one of: instructions for using the labeled probe to image a subject, or subject samples (e.g., cells or tissues), which can be used as an indicator of conditions including, but not limited to, bacterial infection.

Embodiments of this disclosure encompass kits that include, but are not limited to, the labeled probe (e.g., [$^{18}$F]-ethyl maltoside probe or [$^{18}$F]-maltotriose probe) and directions (written instructions for their use). The components listed above can be tailored to the particular biological condition (bacterial infection) to be monitored as described herein. The kit can further include appropriate buffers and reagents known in the art for administering various combinations of the components listed above to the subject. The labeled probe and carrier may be provided in solution or in lyophilized form. When the labeled probe and carrier of the kit are in lyophilized form, the kit may optionally contain a sterile and physiologically acceptable reconstitution medium such as water, saline, buffered saline, and the like.

Dosage Forms

Embodiments of the present disclosure can be included in one or more of the dosage forms mentioned herein. Unit dosage forms of the pharmaceutical compositions (the "composition" includes at least the labeled probe (e.g., [18F]-ethyl maltoside probe or [18F]-maltotriose probe) of this disclosure may be suitable for oral, mucosal (e.g., nasal, sublingual, vaginal, buccal, or rectal), parenteral (e.g., intramuscular, subcutaneous, intravenous, intra-arterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

Typical compositions and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Embodiments of the present disclosure include pharmaceutical compositions that include the labeled probe (e.g., [18F]-ethyl maltoside probe or [18F]-maltotriose probe), pharmaceutically acceptable salts thereof, with other chemical components, such as physiologically acceptable carriers and excipients. One purpose of a pharmaceutical composition is to facilitate administration of labeled probe (e.g., [18F]-ethyl maltoside probe or [18F]-maltotriose probe) to a subject (e.g., human).

Embodiments of the present disclosure may be salts and these salts are within the scope of the present disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when an embodiment of the present disclosure contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds may be formed, for example, by reacting an active compound with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

The amounts and a specific type of active ingredient (e.g., a labeled probe such as [18F]-ethyl maltoside probe or [18F]-maltotriose probe) in a dosage form may differ depending on various factors. It will be understood, however, that the total daily usage of the compositions of the present disclosure will be decided by the attending physician or other attending professional within the scope of sound medical judgment. The specific effective dose level for any particular host will depend upon a variety of factors, including for example, the activity of the specific composition employed; the specific composition employed; the age, body weight, general health, sex, and diet of the host; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

EXAMPLES

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example 1

Despite advance in molecular diagnostics and imaging, the rapid diagnosis of bacterial infections has continued to pose a challenge to the medical community. The last few years have seen the emergence of various positron emission tomography (PET) tracers to image bacterial infection preclinically. These tracers are specific to a certain class of bacteria ([$^{18}$F]-fluorodeoxysorbital for enterobacteriaceae) or can be used to image any bacterial infection like the 6-[$^{18}$F]-fluoromaltose. While these tracers would enable physicians to determine the location(s) and the spread of bacterial infections in patients, they would still not inform on the identity of the bacterial strain that has infected a given individual. In this study we report on the development of a novel PET tracer 6"-[$^{18}$F] fluoromaltotriose that can be used to image all bacterial infections.

6"-[$^{18}$F]-fluoromaltotriose (FIG. 1.1B) was synthesized. The uptake of 6"-[$^{18}$F]-fluoromaltotriose was evaluated in *E. coli*. The accumulation of 6"-[$^{18}$F]-fluoromaltotriose in the *E. coli* increased over time. The uptake in *E. coli* could also be blocked by a co-incubation with 1 mM of cold maltose (98% blocking, p<0.0003), the natural substrate of the transporter, confirming that the tracer was a substrate of the bacterial maltose transporter. $10^8$ colony-forming units (CFU) of *E. coli* was then inoculated in the right thigh muscle of nude mice (n=4). 24 h later, 200 uCi of the 6"-[$^{18}$F]-fluoromaltotriose was administered via tail vein and dynamic PET/CT scans were obtained over the course of one hour. FIG. 1.1A shows a representative PET/CT image at 1 hour. The tracer clearly accumulated in the infected leg. ROI analysis showed that infected muscle had an average uptake of 4.7±1.3% ID/g (mean±SD), 3.1-fold higher than the contra-lateral muscle (p<0.05). The route of clearance of the tracer is renal which makes it suitable for clinical translation.

In this example a tracer that can be used to image all bacterial infections has been synthesized and tested. This tracer has been shown to have exquisite sensitivity and specificity and a clearance pattern that makes it amenable for clinical translation. This tracer will enable clinicians to determine the location and extent of the infection greatly improving the clinical management of infectious diseases.

Example 2

This example demonstrates the use of a positron emission tomography (PET) tracer to visualize and monitor the therapeutic response to bacterial infections. There have been several publications on the use of maltose and maltohexose PET Probes for imaging bacterial infections (Gowrishankar et al, PLOS one 2014 and Ning et al, Angew. Chem. Int. 2014). Both of the published tracers unfortunately had significant background signal particularly in the abdominal region which would make imaging infectious diseases challenging. We therefore continued our efforts to find the second generation of maltose-based PET tracers. We have designed, successfully prepared, and evaluated 6"-[$^{18}$F]fluoromaltotriose as a next-generation bacterial infection PET imaging agent. This tracer show greatly improved pharmacokinetics with predominantly renal clearance making it suitable for clinical translation. FIGS. 5.1A and 5.1B illustrate schemes 1 and 2 that show the synthesis of 6"-[$^{18}$F] fluoromaltotriose.

In regard to FIG. 5.1A, 6"-[$^{18}$F]fluoromaltotriose was synthesized from precursor per-O-acetyl-6"-deoxy-6"-nosyl-maltotriose (1). Precursor 1 was prepared from per-O-acetyl-6"-hydroxymaltotriose via a nosylation reaction. This method utilizes the reaction between the leaving group nosylate in precursor 1 and anhydrous [$^{18}$F]KF/Kryptofix 2.2.2 in acetonitrile at 85° C. for 15 min to give per-O-acetyl-6"-deoxy-6"-[$^{18}$F]fluoromaltotriose (2). Basic hydrolysis of the acetyl protecting groups in 2 yielded 6"-[$^{18}$F] fluoromaltotriose (3). Also, cold 6"-fluoromaltotriose (for comparison with 6" [$^{18}$F]fluoromatotriose) was prepared from per-O-acetyl-6-hydroxymaltotriose via a DAST reaction followed by a basic hydrolysis. Escherichia-coli uptake of 6"-[$^{18}$F]fluoromaltotriose was evaluated in bacterial culture.

In regard to FIG. 5.1B, cold 6"-fluoromaltotriose for comparison with 6"-[$^{18}$F]fluoromatotriose) was prepared from per-O-acetyl-6-hydroxymaltotriose (4) via a DAST reaction in Py/CH$_2$Cl$_2$ followed by a basic hydrolysis ($^{19}$F NMR: −235.9 ppm). Escherichia-coli uptake of 6"-fluoromaltotriose was evaluated in bacterial culture.

We have successfully synthesized 6"-[$^{18}$F]fluoromaltotriose in 4-7% radiochemical yield (decay corrected) with 95% chemical and radio-chemical purities. Total synthesis time was 125 min. Preliminary bacteria uptake experiments showed that E-coli takes up 6"-[$^{19}$F]fluoromaltotriose and the uptake is time dependent. Competition assay indicated that the uptake was blocked by co-incubation with 1 mM of cold maltose (90% blocking, p<0.0003, FIG. 2.1), the natural substrate of the maltose transporter. This observation is consistent with 6"-[$^{18}$F]fluoromaltotriose being recognized and transported by the bacteria in a manner similar to maltose.

This disclosure provides the synthesis of 6"-[$^{18}$F]fluoromaltotriose by a direct fluorination of a protected maltotriose precursor. This methodology can be also used for synthesis of 1-[$^{18}$F]fluoromaltotriose, 2-[$^{18}$F]fluoromaltotriose, 6-[$^{18}$F]fluoromaltotriose and 6'-[$^{18}$F]fluoromaltotriose. 2-[$^{18}$F]-1-fluoroethyl maltoside 3a was synthesized from precursor per-O-acetyl-1-deoxy-ethyl-tosyl-maltose (1a) (FIG. 5.1c). [$^{18}$F]-labeled ethyl maltoside derivative 2a was prepared by nucleophilic reaction of tosylate group in 1a with anhydrous [$^{18}$F]KF/Kryptofix 2.2.2 in DMF at 100° C. for 20 min. Initial purification of [$^{18}$F]2a was performed via a light C-18 Sep-pack cartridge. After passing a solution of [$^{18}$F]2a in acetonitrile through a light neutral alumina Seppack and evaporating the solvent, it was smoothly hydrolyzed t by a base (1N NaOH) at 110° C. for 20 min and then neutralized by 1N HCl to yield [$^{18}$F]-1-fluoroethyl maltoside 3a. The radiochemical yield was 8-10%.

Preliminary bacterial uptake and competition assay experiments in E-coli suggest a possible application of 6"-[$^{18}$F]fluoromaltotriose as a new PET tracer to track and image bacterial infection.

Example 3

FIG. 3.1, example 3, illustrates a graph comparing the biodistribution and pharmacokinetics of 6-fluoromaltose and 6"-Fluoromaltotriose in mice. 6-"fluoromaltotriose has reduced blood, heart, liver, lung and muscle uptake as compared to our first generation tracer making it more suitable to image infections.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are merely set forth for a clear understanding of the principles of this disclosure. Many variations and modifications may be made to the above-described embodiment(s) of the disclosure without departing substantially from the spirit and principles of the disclosure. All such modifications and variations are intended to be included herein within the scope of this disclosure and protected by the following claims.

We claim at least the following:

1. A composition comprising a labeled maltotriose probe, wherein the labeled maltotriose probe includes:

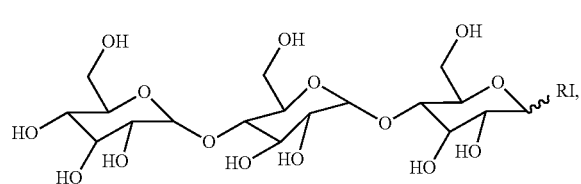

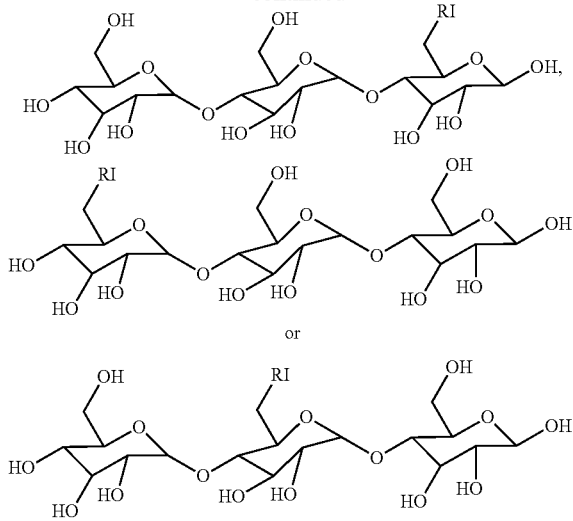

wherein RI is a radiolabel, and wherein the radiolabel is $^{18}$F.

2. The composition of claim 1, wherein the labeled maltotriose probe is 6''-$^{18}$F-maltotriose having the following structure:

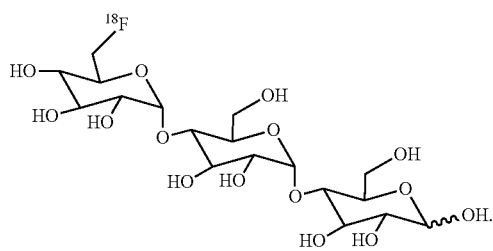 [SMILES: OCC1OC(O)C(O)C(O)C1OC1OC(CO)C(OC2OC(C[18F])C(O)C(O)C2O)C(O)C1O]

3. A method of imaging a bacterial infection in a subject comprising the steps of:
   administering to the subject a labeled maltotriose probe selected from the group consisting of:

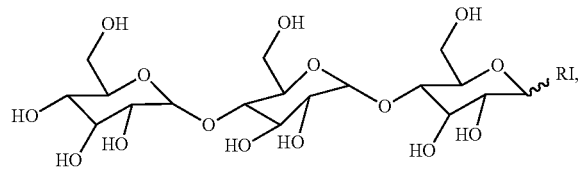

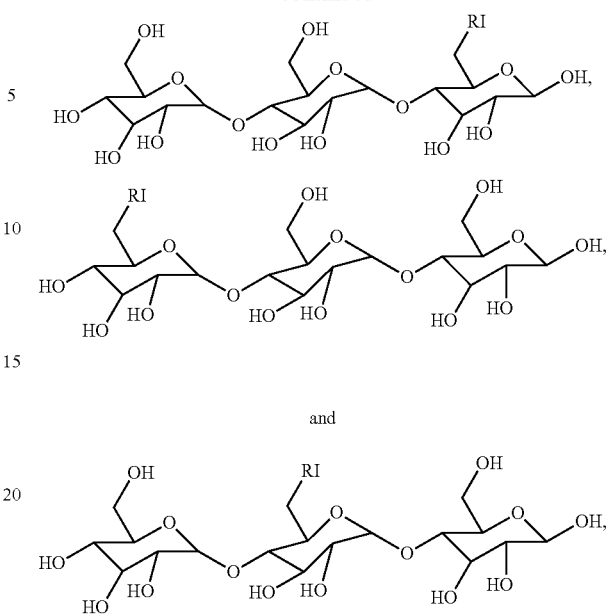

wherein RI is a radiolabel, and wherein the radiolabel is $^{18}$F;
   imaging at least a portion of the subject; and
   detecting the labeled maltotriose probe, wherein the location of the labeled maltotriose probe corresponds to the bacterial infection.

4. The method of claim 3, further comprising repeating the steps of claim 3 periodically to monitor the progress of a bacterial infection in the subject.

5. The method of claim 3, wherein the labeled maltotriose probe is 6''-$^{18}$F-maltotriose having the following structure:

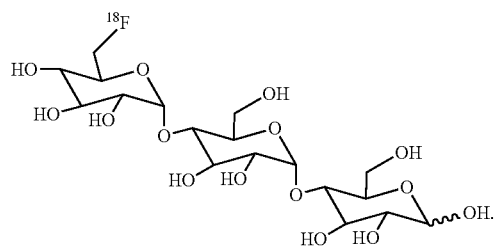 [SMILES: OCC1OC(O)C(O)C(O)C1OC1OC(CO)C(OC2OC(C[18F])C(O)C(O)C2O)C(O)C1O]

* * * * *